US007655237B2

(12) United States Patent
Fernandez-Real et al.

(10) Patent No.: US 7,655,237 B2
(45) Date of Patent: Feb. 2, 2010

(54) USE OF SOLUBLE CD14 FOR TREATMENT OF TYPE 2 DIABETES MELLITUS

(75) Inventors: José Fernandez-Real, Girona (ES); Wifredo Engel, Girona (ES)

(73) Assignee: Bridge Bioresearch Limited, London (GB)

( * ) Notice: Subject to any disclaimer, the term of this patent is extended or adjusted under 35 U.S.C. 154(b) by 496 days.

(21) Appl. No.: 10/550,265

(22) PCT Filed: Feb. 23, 2004

(86) PCT No.: PCT/EP2004/050189

§ 371 (c)(1), (2), (4) Date: Nov. 21, 2006

(87) PCT Pub. No.: WO2004/082578

PCT Pub. Date: Sep. 30, 2004

(65) Prior Publication Data

US 2007/0172477 A1  Jul. 26, 2007

(30) Foreign Application Priority Data

Mar. 21, 2003  (ES) .............................. 200300665
Dec. 16, 2003  (EP) .............................. 03104722

(51) Int. Cl.
*A61K 39/00* (2006.01)
(52) U.S. Cl. ................. 424/185.1; 424/192.1; 530/324
(58) Field of Classification Search ....................... None
See application file for complete search history.

(56) References Cited

U.S. PATENT DOCUMENTS 5,730,975 A * 3/1998 Hotamisligil et al. ..... 424/130.1
5,804,189 A * 9/1998 Goyert .................... 424/185.1
5,869,055 A    2/1999 Juan et al.
6,319,245 B1 * 11/2001 Berrigan .................. 604/891.1

FOREIGN PATENT DOCUMENTS

WO    WO 92/04908          4/1992
WO    WO 92/04908 A1       4/1992
WO    WO 93/19772         10/1993
WO    WO 93/19772 A1      10/1993
WO    WO 00/53165          9/2000
WO    WO 00/53165 A2       9/2000
WO     WO 0053165 A2 *     9/2000

OTHER PUBLICATIONS

The Merck Manual of Diagnosis and Therapy, 17th edition, 1999, Diabetes Mellitus, pp. 165-177.*
The Merck Manual of Diagnosis and Therapy, 17th edition, 1999, Arteriosclerosis, pp. 1654-1659.*
Koenig Wolfgang et al: CD14 C(-260) fwdarwT Polymorphism, Plasma Levels of the Soluble Endotoxin Receptor CD14, their Association with Chronic Infections an Risk of Stable Coronary Artery Disease, Journal of the American College of Cardiology, Jul. 3, 2002, pp. 34-42, vol. 40, No. 1.
Marques-Vidal Pedro et al: Prevalence of Insulin Resistance Syndrome in Southwestern France and its Relationship with Inflammatory and Hemostatic Markers, Diabetes Care, Aug. 2002, pp. 1371-1377, vol. 25, No. 8.
Hubacek J A et al: C(-260) T Polymorphism in the Promoter of the CD14 Monocyte Receptor Gene as a Risk Factor for Myocardial Infarction, Circulation, American Heart Associtation, 1999, pp. 3218-3220, vol. 99, Dallas, TX, US.
Communication under Rule 71(3) EPC, Mar. 20, 2008, European Patent Office.
Decision to Grant a European Patent Pursuant to Article 97(1) EPC, Jul. 31, 2008, European Patent Office.
Koenig, Wolfgang et al., CD14 C(-260) →T Polymorphism, Plasma Levels of the Soluble Endotoxin Receptor CD14, Their Association with Chronic Infections and Risk of Stable Coronary Artery Disease, Journal of the American College of Cardiology, 2002, pp. 34-42, vol. 40, No. 1, Elsevier Science Inc.
Marques-Vidal, Pedro et al., Prevalence of Insulin Resistance Syndrome in Southwestern France and Its Relationship with Inflammatory and Hemostatic Markers, Diabetes Care, Aug. 2002, pp. 1371-1377, vol. 25, No. 8.
Hubacek, Jaroslav A. et al., C(-260) →T Polymorphism in the Promoter of the CD14 Monocyte Receptor Gene as a Risk Factor for Myocardial Infarction, Brief Rapid Communications, 1999, pp. 3218-3220, vol. 99.
Schreyer, Sandra A. et al., Obesity and Diabetes in TNF-α Receptor-deficient Mice, J.Clin.Invest, Jul. 1998, pp. 402-411, vol. 102, No. 2.
Jacob, Chaim O. et al., Prevention of Diabetes in Nonobese Diabetic Mice by Tumor Necrosis Factor (TNF): Similarities Between TNF-α and Interleukin 1, Proc.Natl.Acad.Sci.USA, Feb. 1990, pp. 968-972, vol. 87.
International Search Report for the International Application No. PCT/EP/2004/050189, European Patent Office, Jun. 16, 2005.
Written Opinion of the International Searching Authority for the International Application No. PCT/EP/2004/050189, European Patent Office. Jun. 14, 2005.
Communication Pursuant to Article 96(2) EPC, Dec. 19, 2006, European Patent Office.
Reply to Examination Report, Amended Claims and General Enquiry, Jun. 20, 2007.

* cited by examiner

*Primary Examiner*—Michael Szperka
(74) *Attorney, Agent, or Firm*—Peter B. Scull; Kristina M. Kalan; Berebbaum Weinshienk PC

(57) ABSTRACT

Use of soluble CD14 (sCD14) for the manufacture of a medicament for therapeutic or preventive treatment of a disease involving a chronic inflammation condition and a clinical disorder associated with insulin resistance in an animal or a human. Examples of diseases include type 2 diabetes mellitus, obesity, metabolic syndrome, arteriosclerotic disease, arterial hypertension and functional ovaric hyperandrogenism.

10 Claims, No Drawings

SEQUENCE LISTING

```
<160> NUMBER OF SEQ ID NOS: 1

<210> SEQ ID NO 1
<211> LENGTH: 26
<212> TYPE: PRT
<213> ORGANISM: mammalian

<400> SEQUENCE: 1

Ala Glu Leu Gln Gln Trp Leu Lys Pro Gly Leu Lys Val Leu Ser Ile
1               5                   10                  15

Ala Gln Ala His Ser Leu Asn Phe Ser Cys
            20                  25
```

USE OF SOLUBLE CD14 FOR TREATMENT OF TYPE 2 DIABETES MELLITUS

CROSS-REFERENCE TO RELATED APPLICATIONS

The present invention claims priority from the Spanish Application Number P200300665 filed 21 Mar. 2003, entitled "New Therapeutic Applications of the Glycoprotein sCD14" (as translated from the Spanish original title); and the European Patent Application No. EP 03104722.8, filed 16 Dec. 2003, entitled "Use of Soluble CD14 for Treatment of Diseases"; the subject matter of each of which hereby being specifically incorporated herein by reference for all that they disclose and teach.

FIELD OF THE INVENTION

The present invention relates to use of soluble CD14 (sCD14) for the manufacture of a medicament for therapeutic or preventive treatment of a disease involving a chronic inflammation condition and a clinical disorder associated with insulin resistance in an animal or a human.

BACKGROUND OF THE INVENTION

The protein, CD14, is a myeloid cell-surface glycoprotein which acts as a receptor for bacterial lipopolysaccharide (LPS). It is well documented that monocyte/macrophage activation by lipopolysaccharides via membrane CD14 (mCD14) triggers the release of a variety of pro-inflammatory, immunoregulatory and cytotoxic molecules such as TNF-$\alpha$, IL-1, IL-6, IL-8, oxygen radical products and nitric oxide. mCD14 is anchored to the cell membrane by a glycosyl-phosphatidylinositol linkage.

In addition to the membrane bound form, soluble CD14 (sCD14) has been identified in normal human blood serum, hereinafter referred to as sCD14. sCD14 exists in two forms, sCD14a (49 kDa) and sCD14p (55 kDa). It has been demonstrated that sCD14 binds LPS and mediates the LPS-induced activation of cells that lack mCD14, including epithelial and endothelial cells and astrocytes, as well as mCD14 expressing cells, such as monocytes and neutrophils. The main source of sCD14 in normal human plasma is the monocyte. A substantial concentration of sCD14 is found in normal human plasma, 2-4 µg/ml.

LPS is believed to be a primary cause of death in humans afflicted with gram-negative sepsis. Sepsis may be defined as a toxic condition resulting from the spread of bacteria or their products from a focus of infection.

Numerous documents in the art describe use of sCD14 or variants/fragments of sCD14 for treatment of sepsis, gram negative bacteria or other related diseases that may be characterized as diseases involving acute inflammation conditions. See e.g. WO9101639, WO92204908, WO9319772, U.S. Pat. No. 5,804,189, WO9620957 and U.S. Pat. No. 5,869,055.

According to the art acute condition may be defined as conditions that are severe and sudden in onset. Symptoms appear, change, or worsen rapidly. A chronic condition, by contract, is continuous or persistent/maintained over an extended period of time. A chronic condition is one that is long-standing, not easily or quickly resolved.

With respect to involvement of sCD14 in diseases involving chronic inflammation, there have been published some studies.

A polymorphism of the CD14 gene, a C-to-T transition at bp-159 from the major transcription start site, seems to play a role in regulating serum sCD14 levels.

The article (Wolfgang K, et al, Journal of the American College of Cardiology, United States—3 Jul. 2002, Vol 40, Nr 1, page 34-42) investigated this polymorphism. They investigated the association of CD14 genotype and plasma levels of soluble sCD14 with risk of stable coronary artery disease (CAD), chronic infections and sensitive markers of systemic inflammation. They found that "sCD14-plasma levels were higher in subjects with TT genotype compared with those with CT or CC genotype (p=0.005)". Based on analysis of the found individual data the abstract concludes "These results do not confirm an independent relationship between CD14 genotypes or plasma levels of sCD14 and risk of stable CAD in this population".

Fernandez-Real J M et al published a poster 12 of September 2001 at RASD meeting in Glasgow. The title was "A polymorphism of the CD14 Monocyte Receptor Gene, involved in the inflammatory cascade, is associated with insulin sensitivity". The abstract reads "C/C type 2 [diabetic] homozygote patients also showed a significant lower insulin sensitivity index than carriers of the T allele".

SUMMARY OF THE INVENTION

The problem to be solved by the present invention is to provide an alternatively new medical use for sCD14.

The solution is based on the hypothesis that LPS produces insulin resistance in humans by a mechanism involving the activation of the inflammatory cascade. Since sCD14 can block the LPS activity the present inventors then investigated whether or not sCD14 could be used for therapeutic or preventive treatment of diseases involving chronic inflammation conditions and insulin resistance.

Based on detailed work (see working examples herein) the present inventors found that by administrating sCD14 it was possible to improve the insulin resistance of the subjects having these diseases. When insulin resistance is improved the subject can better use it and the blood glucose levels can then better be normalized For example in example 1 this is demonstrated for subjects (diabetic mice) with type 2 diabetes and in example 4 this is demonstrated for subjects (mice) with obesity. It is well established that nice are good model animals for corresponding effects in human.

Accordingly, a first aspect of the invention relates to use of sCD14 for the manufacture of a medicament for therapeutic or preventive treatment of a disease involving a chronic inflammation condition and a clinical disorder associated with insulin resistance in an animal or a human.

This first aspect may alternatively be formulated as a method for therapeutic or preventive treatment of a disease involving a chronic inflammation condition and a clinical disorder associated with insulin resistance in an animal or a human comprising administering to an animal or a human in need thereof an effective amount sCD14.

An advantage of using sCD14 is that it improves insulin resistance and thereby normalizes blood glucose levels. On the contrary, if insulin is given to e.g. type 2 diabetes patients the glucose levels go down in a more uncontrollable manner. Said in another way, one has to continuously and precisely control the amount of administrated insulin and continuously monitor the concentrations of glucose in order not to get too low glucose levels. Since sCD14 merely normalizes the glucose level the risk of too low glucose levels is absent. This offers the possibility of e.g. administrating the sCD14 as a depot (e.g. an injectable depot) to the patient The depot can be made with an adequate release profile of sCD14 and the patient can thereby, in a comfortable easy way, get a continued improved insulin resistance and thereby continued normalized blood glucose levels. See below for further details.

Embodiment(s) of the present invention is described below, by way of example(s) only

DETAILED DESCRIPTION OF THE INVENTION

Discussion of Theory Behind Use of sCD14

The studies made by the present inventors demonstrate that there exists a negative correlation between the serum concentrations of sCD14 and parameters relating to insulin resistance, obesity and hypertension in healthy men. The studies firer indicate that persons with obesity have relatively lower serum sCD14 concentrations and, in persons with type 2 diabetes, the concentrations of circulating sCD14 are inversely associated with the degree of vascular dysfunction.

Studies in experimental animals show that administration of human recombinant sCD14 to diabetic mice (ob/ob) decrease the basal glycemia (the presence of glucose in the blood) without producing changes in body weight, the weight of the soleus muscles, the weight of the epidermal adipose tissue or in the ingestion of food. Similar positive results have been observed after administration of human recombinant sCD14 to mice with obesity.

In summary, the discoveries of the present inventors demonstrate that the serum concentrations of sCD14 is decreased in persons with obesity, is directly proportional to the insulin sensitivity in healthy persons and inversely proportional to the degree of vascular dysfunction in diabetic type 2 patients. This clearly indicates that sCD14 is a protein that is capable of protecting against negative development of insulin resistance and the vascular alternations associated to this. This conclusion is supported by the effect of lowering/normalizing the blood glucose levels (without modification of weight and ingestion of food) that have been observed after administration of human recombinant sCD14 in diabetic mice (see example 1 herein) and in mice with obesity (see example 4).

Suitable sCD14:

Suitable sCD14 that can be used according to the invention may be soluble sCD14 from a mammalian, in particular recombinant human sCD14 or any protein or substance that comprises following amino acid sequence (SEQ ID NO 1):

AELQQWLKPGLKVLSIAQAHSLNFSC

This amino acid sequence is a fragment of recombinant human sCD14. It comprises amino acids 143 to 168 of the human sCD14 sequence. See U.S. Pat. No. 5,804,189, column 18 for further details.

Alternatively expressed, suitable sCD14 that can be used according to the invention may be recombinant human sCD14 or a fragment, a variant or a mammalian sCD14 homolog thereof, wherein the fragment the variant or the mammalian homolog have LPS binding properties corresponding to the recombinant human sCD14.

The art describes cloning of a number of mammalian sCD14. Recombinant production of human sCD14 is also well known in the art See e.g. U.S. Pat. No. 5,804,189.

Suitable fragments of sCD14 are e.g. described in U.S. Pat. No. 5,804,189 and U.S. Pat. No. 5,869,055. U.S. Pat. No. 5,869,055 describes sCD14 variants comprising an amino acid sequence that begins with one of amino acids 1 through 6 and ends with one of amino acids 152 through 348 of SEQ ID NO:38 [soluble human CD14 having 348 amino acids], wherein Xaa Xaa Xaa Xaa are each independently selected from the group consisting of Gly, Ala, Val, Leu, Ile and Pro.

In order to test LPS binding properties it is preferred to use a competitive LPS binding assay. A suitable assay is described in U.S. Pat. No. 5,804,189, column 18. Briefly, sCD14 (100 μl/well, 16 μg/ml) is added to ELISA plates. The wells are blocked with 0.5% gelatin diluted in PBS. Serial dilutions of the sCD14 are made in PBS containing 0.1% gelatin and added to biotinylated LPS (final concentration, 1 μg/ml). Purified rabbit LBP is also added (final concentration, 1 μg/ml). The samples are incubated for 30 min at 37° C. and are then added to the sCd14-coated wells and the plates are incubated 4 h at 37° C. Bound LPS is detected using a streptavidin-alkaline phosphatase detection system For further details see U.S. Pat. No. 5,804,189.

Preferably, in such a competitive LPS binding assay, a fragment, a variant or a mammalian sCD14 homolog it said to have sCD14 LPS binding properties corresponding to the recombinant human sCD14 if it has LPS binding properties at least corresponding to a peptide consisting of the amino acid sequence given above. Data of binding properties for such a peptide is given in FIG. 8 of U.S. Pat. No. 5,804,189.

More preferably, a fragment, a variant or a mammalian sCD14 homolog it said to have sCD14 LPS binding properties corresponding to the recombinant human sCD14 if it has LPS binding properties at least corresponding to the recombinant human sCD14. Data of binding properties for the recombinant human sCD14 is given in FIG. 8 of U.S. Pat. No. 5,804,189.

In short, the data shown in FIG. 8 of U.S. Pat. No. 5,804,189 are following. The data is plotted as % maximal response. The recombinant human sCD14 appears to inhibit more efficiently at lower concentrations, however, at the higher concentration (1.7 μM), peptide inhibits almost as well (72%) as recombinant human sCD14 (84%). When the peptide is used at a concentration of 7 μM, the amount of inhibition (84%) is the same as that achieved with 1.7 μM of recombinant human sCD14.

As known to the skilled person, it may be preferred to administer an active ingredient as physiologically acceptable salts. Accordingly, within the term sCD14 is also included physiologically acceptable salts of the sCD14.

Disease Involving a Chronic Inflammation

Suitable examples of diseases involving a chronic inflation condition are the type 2 diabetes mellitus, obesity, metabolic syndrome (a group of manifestations characterized by one or several of the following symptoms: insulin resistance, dyslipidemia, obesity, arterial hypertension, coagulation alternations or hyperuricemia), arteriosclerotic disease, arterial hypertension, functional ovaric hyperandrogenism, dyslipidemia and any other disease state that is associated with insulin resistance.

Clinical symptoms of all the mentioned disease are in one way or the other known to be associated with some kind insulin resistance.

It is within the general knowledge of the skilled person to identify if e.g. a human has one of the diseases above. Reference is e.g. made to the National Library of Medicine, USA (NLM) website: (http://www.nlm.nih.gov), where details of these diseases are described.

At this site is e.g. metabolic syndrome described as "a collection of health risks that increase your chance of developing heart disease, stroke, and diabetes. The condition is also known by other names including Syndrome X insulin resistance syndrome, and dysmetabolic syndrome. According to a national health survey, more than one in five Americans has metabolic syndrome. The number of people with metabolic syndrome increases with age, affecting more than 40 percent of people in their 60s and 70s."

Administration of sCD14

According to the teaching of the present invention sCD14 can be administered to animals and humans for therapeutic or preventive treatment of a disease involving a chronic inflammation condition. The purpose of the administration of sCD14 may be preventive (to avoid the development of these diseases) and/or therapeutic (to treat these diseases once they have been developed/installed). Preferably the sCD14 is administered to a human. If administrated to an animal is it preferred that the animal is a mice.

Preferably sCD14 is administered at doses of about 0.1 to 100 µg/kg of body weight, preferably at a level of about 1 to 50 µg/kg of body weight, and the amount may be administered, e.g., in divided doses on daily basis. The particular dose may be varied within or without the range that is specified herein depending on the particular application or severity of a disease. Those who are skilled in the art may ascertain the proper dose using standard procedures. It is understood that the dose should be an effective amount of sCD14 in the sense that improved insulin resistance is seen in the treated subject Suitable assay for testing improved insulin resistance is known to the skilled person and guidance may be found in the working examples herein.

According to common general knowledge it is understood that the medicament may be in the form of a pharmaceutical composition. Such medicament/pharmaceutical composition may be administered by any means that achieve their intended purpose. For example, administration may be by parenteral routes, including subcutaneous, intravenous, intradermal, intramuscular, intraperitoneal, intrathecal, transdermal, or buccal routes. Alternatively, or concurrently, administration may be by the oral or rectal route. The pharmaceutical compositions can be administered parenterally by bolus injection or by gradual release over time.

As explained above, since sCD14 merely normalizes the glucose level the risk of too low glucose levels is absent. This offers the possibility of e.g. administrating the sCD14 as a depot (e.g. an injectable depot composition) to the patient The depot can be made with an adequate release profile of sCD14 and the patient can thereby, in a comfortable easy way, get a continued improved insulin resistance and thereby continued normalized blood glucose levels.

Accordingly, in a preferred embodiment the medicament comprises a depot composition, more preferably an injectable depot composition. After introduction into the patient (animal or human), the depot shall preferably have an adequate release profile of sCD14. Numerous suitable depot compositions are know to the skilled person and can be made with various adequate release profiles. See e.g. U.S. Pat. No. 6,331, 311 with title "Injectable depot gel composition and method of preparing the composition" for further details with respect to suitable depot compositions.

Preferably, the injectable depot composition is an injectable depot gel composition. Preferably, the depot composition is administered by implanting, preferably subcutaneously, a suitable device. An example of such a suitable device is so-called pumps. A suitable example of this is the commercial available ALZET® Osmotic Plumps from the company DURECT Corporation, USA. Suitable adequate pumps are known to the skilled person and they provide the possibility of providing continuous delivery (preferably by subcutaneously implantation), thereby eliminating the need for frequent, round-the-clock injections.

Adequate release profiles could e.g. be a release profile allowing the depot to be administrated in a period interval from between each 14 days to each 3 month.

In addition to sCD14, the pharmaceutical compositions may contain suitable pharmaceutically acceptable carriers comprising excipients and auxiliaries which facilitate processing of the active compounds into preparations which can be used pharmaceutically. Preferably, the preparations, particularly those which can be administered orally and which can be used for the preferred type of administration, such as tablets, dragees, and capsules, and also preparations which can be administered rectally, such as suppositories, as well as suitable solutions for administration by injection or orally, contain from about 0.1 to about 99 percent, preferably from about 25-85 percent, of active compound(s), together with the excipient.

Suitable excipients are, in particular, fillers such as sugars, such as lactose, sucrose, mannitol, or sorbitol; cellulose preparations and/or calcium phosphates, such as tricalcium phosphate or calcium hydrogen phosphate; as well as binders such as starch paste made using, for example, maize starch, wheat starch, rice starch, potato starch, gelatin, gum tragacanth, methyl cellulose, hydroxypropylmethylcellulose, sodium carboxymethyl cellulose, and/or polyvinylpyrrolidone. If desired, disintegrating agents may also be added, such as the above-mentioned starches as well as carbomethyl starch, cross-linked polyvinyl pyrrolidone, agar, or alginic acid or a salt thereof, such as sodium alginate. Auxiliaries which can be used in the compositions according to the present invention include flow-regulating agents and lubricants such as silica, talc, stearic acid or salts thereof, a detergent such as Triton, and/or polyethylene glycol.

EXAMPLES

Example 1

Treatment of Insulin-Resistant Diabetic C57BL/6J ob/ob Mice with Human Recombinant Soluble CD14.

The objective of this experiment was to study the effect of systemic administration of human recombinant sCD14 (rhCD14) with respect to relevant insulin resistance parameters in experimental mice (mice C57BL/6J ob/ob).

Materials and Methods:

Experimental animals: Mice strains C57BL/6J ob/ob (The Jackson lab.). Males of 10 weeks old. These animals had obesity with hyperphagia, hyperinsulinemia (the presence of excess insulin in the blood), insulin resistance and moderate hyperglycemia (an excess of sugar in the blood).

Treatment of the mice with rhCD14: rhCD14 was continuously infused for 12 days by use of Alzet® pumps (pump 1002, 100 µl) implanted subcutaneously on the back of the animals. 20 mice were used. 10 with rhCD14 and 10 with saline serum (control). The dose was 1 µg/g weight of mice/day and it was administrated subcutaneously for 12 days.

Assay for glucose tolerance: Finalized the 12 days and after 16 hours of fasting, an intraperitoneal glucose tolerance test (GTT) was made. 2 g/kg of glucose (Glucosmon, 50%) were injected intraperitoneally. Blood samples were taken from the tail of the mice (20 µl) at 0, 15, 30, 60, 120 and 180 minutes after the glucose administration. The blood glucose levels were measured using a conventional glucometer (Menarini) and the insulin levels were meed by ELISA (Mercodia Ultrasensitive Mouse Insulin ELISA).

Results:

Following results were obtained:

The treatment with rhCD14 did not produce significant changes, between treated and controls, in body weight, the weight of the soleus muscles, the weight of the epidermal adipose tissue or in the ingestion of food.

The treatment with rhCD14 decreased the basal levels of serum glucose compared to the control group. Values represent mean±SEM. Two-way ANOVA test indicated a significant difference (P<0.02) between the glucose curves of control and hCD14 treated mice. Fasting blood glucose values were statistically different: 242±30 mg/dL in control vs 153±14 mg/dL in hCD14 treated mice, P=0.02.

The concentrations of serum insulin also decreased concomitantly with the decrease of the serum glucose in mice treated with rhCD14. However, it did not decrease so significantly as glucose did. Two-way ANOVA test indicated a significant difference (P<0.0001) between the insulin curves of control and hCD14 treated mice.

In summary, these results make it possible to conclude that rhCD14 has a positive effect with respect to normalization of blood glucose levels in the diabetic C57BL/6J ob/ob mice. Since the glucose levels decrease significantly and the insulin levels are not increased (decrease relative less than for glucose) it is highly probably due to in improved insulin sensitivity (e.g. less insulin resistance).

Example 2

Relation Between sCD14 Serum Concentrations and Obesity

The objective of this example was to study the sCD14 serum concentrations in relation to the degree of obesity and inflammatory parameters in healthy subjects. The basic hypothesis was that sCD14, which circulates in high concentrations in a constitutive manner in the plasma, plays an important part in the neutralization of LPS. The mRNA of CD14 has been found in the adipose tissue and the cells of the immune system.

Methods:

The sCD14 concentrations were measured (EASIA, enzyme amplified solid immune assay) in relation to anthropometries measures and inflammatory parameters (soluble fractions of tumor necrosis factor-alpha receptors 1 and 2, TNFR1s and TNFR2s, EASIA) in healthy subjects.

Results:

The sCD14 serum concentrations did not significantly correlate with the body mass index (BMI) in the global analysis of the subjects (r=0.06, p=0.30, n=229). However, in lean patients (BMI<25, n=100), the sCD14 was significantly associated with the BMI (r=0.36, p<0.0001). These observations were not found in obese patients (r=0.03, p=0.67). Impressive results were observed between the sCD14 and TNFR2 concentrations in obese subjects but not in lean subjects. An inverse association was found between both parameters (r=−0.26, p<0.01, and r=0.01, p=0.87, respectively). The subjects with BMI higher than 30 kg/m$^2$ had lower sCD14 concentrations (4.41±1.5 compared to 4.83±1.2; p=0.01).

The lower concentrations of sCD14 in obese subjects could indicate an increase of the inflammatory activity due to its crucial importance with respect to neutralization of the LPS.

Example 3

Relation Between sCD14 Serum Concentrations and Insulin Resistance

The objective of this study was to analyze the plasmatic sCD14 and the C-159T polymorphism in relation to parameters of insulin resistance in healthy subjects and patients with type 2 diabetes mellitus. The basic hypothesis was that sCD14, which circulates at high concentrations in a constitutive manner in the plasma, plays an important part in the neutral on of LPS. A polymorphism in the gene of CD14 (a transition C—T in position −159), could play an important part in the regulation of the circulating concentrations of sCD14.

Methods:

The serum sCD14 concentrations (using EASIA) and the polymorphism of the CD14 gene in 123 healthy subjects and in 32 patients with diabetes type 2 were measured. In the subgroup of the 32 patients a glucose oral tolerance test (OGTT) and a frequently sampled intravenous glucose tolerance test were also performed.

Results:

In the table below are shown the data corresponding to the anthropometries and analytical variables of the control subjects.

In males, the sCD14 serum concentrations, adjusted with respect to the triglyceride concentrations, significantly correlated with the basal insulinemia (r=−0.25, p=0.029), the basal index for insulin resistance (FIRI, r=−0.28, p=0.014) and the circulating uric acid (r=−0.30, p=0.006). In non smoking males (n=44), the sCD14 significantly correlated with the abdominal perimeter (r=−0.30, p=0.03), the FIRI (r=−0.30, p=0.03), the systolic arterial pressure (r=−0.32, p=0.029) and the diastolic arterial pressure (r=−0.34, p=0.022). A multiple linear regression analysis to predict FIRI was also performed. In this analysis, the BMI (p<0.00001), the basal triglyceride concentrations (p=0.003) and the sCD14 (p=0.04), but not the age, sex, abdominal perimeter nor smoking status, contributed in an independent manner to 26% of the FIRI variance.

Healthy homozygote C/C subjects had a similar distribution of age, sex, BMI fat mass, waist-hip index, arterial pressure, basal glucemia and basal insulinemia, in relation to subject bearing an T allele. However, the C/C subjects had higher integrated concentrations of glucose during the OGTT (ABC glucose; p=0.02) and lower index for insulin sensitivity compared to the subjects bearing an allele T.

Diabetic homozygote C/C patients had a lower insulin sensitivity index (p=0.03) and higher concentrations of C reactive protein and ICAM-1 (p=0.01) in comparison with diabetic carriers of the T allele.

Accordingly, an association between the circulating concentrations of sCD14, and an allelic variant of its gene, with parameters of insulin resistance in healthy subjects and in patients with type 2 diabetes mellitus were observed. Furthermore, an effect of the genetic polymorphism on insulin sensitivity and on endothelial function (ICAM-1s) in patients with type 2 diabetes mellitus were observed.

TABLE anthropometries and analytical variables of the control subjects.

| Variable | C/C | C/T and TT | P |
|---|---|---|---|
| N | 20 | 41 | — |
| Males/Females | 13/7 | 25/16 | NS |
| Age(years) | 40.1 ± 8.5 | 38.7 ± 9.5 | NS |
| Corporal mass index (Kg/m$^2$) | 27.7 ± 4.7 | 27.1 ± 5.2 | NS |
| Fat mass (kg) | 21.7 ± 12.6 | 19.6 ± 13.1 | NS |
| Free fat mass | 60.1 ± 10.8 | 59.4 ± 11.8 | NS |
| Relation waist-hip | | | |
| Males | 0.96 ± 0.03 | 0.98 ± 0.04 | NS |
| Females | 0.91 ± 0.1 | 0.92 ± 0.09 | NS |
| Systolic arterial pressure | 124.1 ± 13.6 | 124.7 ± 10.7 | NS |
| Diastolic arterial pressure | 74.1 ± 10 | 73.1 ± 9.6 | NS |
| Tympanic temperature (° C.)(n = 28) | 35.6 ± 0.4 | 35.7 ± 0.4 | NS |
| Peripheral leucocytes (×10$^9$/ml) | 6926 ± 1194 | 6897 ± 1751 | NS |
| TNFR1s (ng/ml) | 1.93 ± 0.57 | 1.84 ± 0.50 | NS |
| TNFR2s (ng/ml) | 3.58 ± 0.86 | 3.45 ± 1.07 | NS |
| Basal glucemia (mmol/l) | 5.2 ± 1.04 | 5.1 ± 0.8 | NS |
| Basal insulinemia (mU/l) | 11.2 ± 6.6 | 9.3 ± 4.7 | NS |
| sCD14 (µg/ml) | 3.57 ± 12 | 3.55 ± 1.7 | NS |
| ABC glucose* during OGTT (mmol/l) | 10.5 ± 3.6 | 7.9 ± 2.4 | 0.022 |
| ABC insulin* during OGTT (mU/l) | 90.8 ± 61.5 | 81.1 ± 60.1 | NS |
| Insulin sensitivity OGTT* (mg*L$^2$/mmol*mU*min) | 35.2 ± 10.2 | 47.7 ± 15.4 | 0.033 |
| Insulin sensitivity* (min$^{-1}$/mU/l) | 1.42 ± 1.1 | 2.64 ± 1.5 | 0.036 |

ABC, area below the curve;
OGTT: glucose oral tolerance assay.
*n = 33 (9 homozygote C/C and 24 bearing the allele T).

Example 4

Treatment of Insulin-Resistant Obese C57BL/6J Mice (HF Mice) with Human Recombinant Soluble CD14.

The objective of this experiment was to study the effect of systemic administration of human recombinant sCD14 (rhCD14) with respect to relevant insulin resistance parameters in experimental mice (C57BL/6J mice (HF mice).

Materials and Methods:

Experiential animals: Male mice strains C57BL/6J (HF mice) C(he Jackson lab.). These animals had obesity.

Treatment of the mice with rhCD14: Male C57BL/6J mice were fed a HF diet (Harlan Teklad No. 88137: 21% by wt and 42% kcal from fat) for 26-28 weeks. The last 12 days, mice received a dose of 1 µg/g bw per day of hCD14 in two injections (0.5 µg/g each one) every 12 hours. The control group was treated with vehicle (saline serum) alone. Each group contained 9 mice.

Assay for Glucose Tolerance: As in Example 1.

Results:

Following results were obtained:

The treatment with rhCD14 did not produce significant changes, between treated and controls, in body weight, the weight of the soleus muscles, the weight of the epidermal adipose tissue or in the ingestion of food.

The treatment with rhCD14 decreased the basal levels of serum glucose compared to the control group. Two-way ANOVA test indicated a significant difference (P<0.002) between the glucose curves of control and rhCD14 treated mice.

The concentrations of serum insulin increased concomitantly with the decrease of the serum glucose in mice treated with rhCD14. However, it did not increase so significantly as glucose decreased. Two-way ANOVA test indicated a significant difference (P<0.0001) between the insulin curves of control and hCD14 treated mice.

In summary, these results make it possible to conclude that rhCD14 has a positive effect with respect to normalization of blood glucose levels in the C57BL/6J HF obesity mice treated with hCD14. Since the glucose levels decrease significantly and the insulin levels are only increased slightly it is highly probably due to in improved insulin sensitivity (e.g. less insulin resistance).

The invention claimed is:

1. A method for therapeutically treating a disease involving a chronic inflammation condition and a clinical disorder associated with insulin resistance in an animal or a human, the disease being type 2 diabetes mellitus; the method including administering soluble CD14 (sCD14) to the animal or human and treating the disease.

2. The method of claim 1, wherein the sCD14 is human sCD 14.

3. The method of claim 1, wherein the sCD14 comprises the amino acid sequence of SEQ ID NO 1.

4. The method of claim 1, wherein the operation of administering soluble CD14 (sCD 14) includes using an injectable depot composition including sCD 14.

5. The method of claim 4, wherein the injectable depot composition is administered by implanting a suitable delivery device in the animal or human.

6. The method of claim 4, wherein the delivery device is implanted subcutaneously.

7. The method of claim 4, wherein the delivery device is a pump.

8. The method of claim 4 wherein the injectable depot composition has an adequate release profile of sCD 14 after introduction into the animal or human.

9. A method for therapeutic treatment of a disease involving a chronic inflammation condition and a clinical disorder associated with insulin resistance in an animal or a human; the method comprising administering to an animal or human in need thereof an effective amount of soluble CD14 (sCD 14); wherein the disease is type 2 diabetes mellitus.

10. The method of claim 9, wherein the soluble CD14 (sCD14) is administered using an injectable depot composition, the injectable depot composition having an adequate release profile of sCD 14 after introduction into the animal or human.

* * * * *

UNITED STATES PATENT AND TRADEMARK OFFICE
CERTIFICATE OF CORRECTION

| | | |
|---|---|---|
| PATENT NO. | : 7,655,237 B2 | Page 1 of 1 |
| APPLICATION NO. | : 10/550265 | |
| DATED | : February 2, 2010 | |
| INVENTOR(S) | : José Fernandez-Real | |

It is certified that error appears in the above-identified patent and that said Letters Patent is hereby corrected as shown below:

On the Title Page, under item [86], § 371 should read:

§ 371 (c)(1), (2), (4) Date:   Sep. 21, 2005

Title Page, item [74] should read Attorney, Agent or Firm – Peter B. Scull; Kristina M. Kalan; Berenbaum Weinshienk PC Signed and Sealed this Thirteenth Day of April, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,655,237 B2 | |
| APPLICATION NO. | : 10/550265 | |
| DATED | : February 2, 2010 | |
| INVENTOR(S) | : José Fernandez-Real et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 717 days.

Signed and Sealed this

Twenty-eighth Day of December, 2010

David J. Kappos
*Director of the United States Patent and Trademark Office*